(12) United States Patent
Ye et al.

(10) Patent No.: US 9,017,332 B2
(45) Date of Patent: Apr. 28, 2015

(54) SURGICAL MILLING CUTTER

(75) Inventors: Lei Ye, Chongqing (CN); Jian Zhou, Chongqing (CN); Hua Feng, Chongqing (CN); Fei Li, Chongqing (CN); Hengyang Zhu, Chongqing (CN); Congxiao Li, Chongqing (CN)

(73) Assignee: Chongqing Runze Pharmaceutical Co., Ltd., Chongqing (CN)

( * ) Notice: Subject to any disclaimer, the term of this patent is extended or adjusted under 35 U.S.C. 154(b) by 199 days.

(21) Appl. No.: 13/823,065

(22) PCT Filed: Sep. 15, 2011

(86) PCT No.: PCT/CN2011/079701
§ 371 (c)(1),
(2), (4) Date: Mar. 13, 2013

(87) PCT Pub. No.: WO2012/068917
PCT Pub. Date: May 31, 2012

(65) Prior Publication Data
US 2013/0274749 A1 Oct. 17, 2013

(30) Foreign Application Priority Data
Nov. 26, 2010 (CN) .......................... 2010 1 0560283

(51) Int. Cl.
*A61B 17/00* (2006.01)
*A61B 17/16* (2006.01)
*A61B 17/32* (2006.01)

(52) U.S. Cl.
CPC ........... *A61B 17/16* (2013.01); *A61B 17/32002* (2013.01); *A61B 17/162* (2013.01); *A61B 17/1624* (2013.01); *A61B 2017/1602* (2013.01)

(58) Field of Classification Search
CPC ................. A61B 17/320016; A61B 17/32002; A61B 17/320783; A61B 2017/320024; A61B 2017/320032; A61B 2017/320791; B23B 31/32; B23B 31/1071
USPC .................... 606/170–171, 180, 167; 279/75; 464/169; 403/353, 348, 364
See application file for complete search history.

(56) References Cited

U.S. PATENT DOCUMENTS

| | | | | |
|---|---|---|---|---|
| 2,598,780 A | * | 6/1952 | Georges | 464/147 |
| 2006/0122640 A1 | * | 6/2006 | Gordon et al. | 606/180 |
| 2011/0225789 A1 | * | 9/2011 | Darnell | 29/428 |

* cited by examiner

*Primary Examiner* — Todd Manahan
*Assistant Examiner* — Erich Herbermann

(57) ABSTRACT

A surgical milling cutter includes a milling cutter holder, a locking device, a locking seat, and a main machine. The milling cutter holder includes a fixing seat with a through hole. A finger guider with an L-type holder on a top end thereof is arranged at an upper part of the fixing seat. A distal end of a short side of the L-type holder is disposed with a downward projection, and a lowest point of the projection is lower than that of a cylindrical head when the milling cutter works normally. A bolt with a central through hole is fixed in a cavity of the finger guider. A pressing disk is arranged at the upper part of the fixing seat, and a nut is connected to the bolt through a hole in the pressing disk.

11 Claims, 7 Drawing Sheets

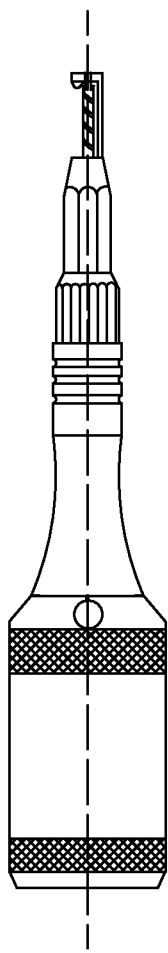
F I G. 1

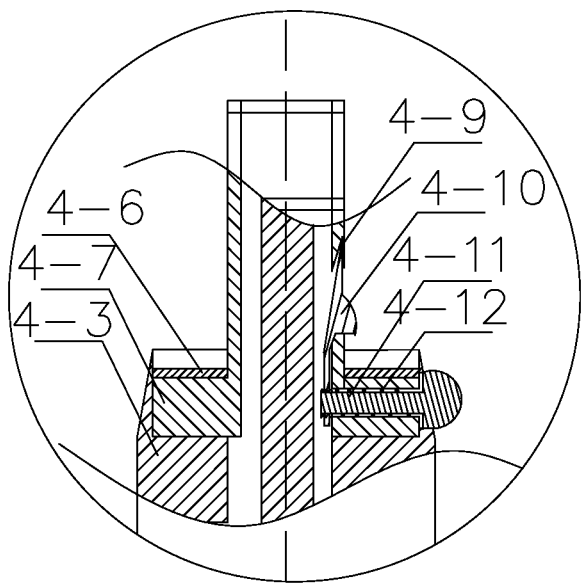
F I G. 8
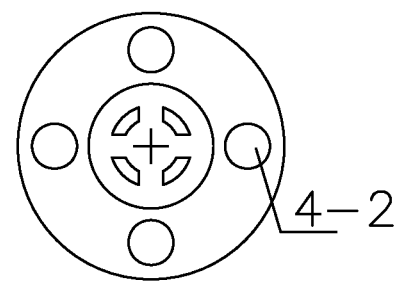
F I G. 9

SURGICAL MILLING CUTTER

BACKGROUND OF THE INVENTION

1. Field of the Invention

The present invention relates to a surgical cutting machine, and more particularly to a surgical milling cutter.

2. Description of the Prior Art

During a surgical operation, a milling cutter is used for cutting. The milling cutter comprises a milling cutter holder, a locking device, a locking seat and a main machine. The top of the milling cutter holder has an L-shaped holder. The short side of the L-shaped hole has a hole. The cylindrical head at the front part of the blade of the milling cutter extends into the hole to ensure that the milling cutter provides a better effect. In order to protect the milling cutter, the cylindrical head doesn't fully extend into the hole so a portion of the cylindrical head is exposed. In the existing technology, the short side of the L-shaped holder is a flat configuration. When cutting an object, the cylindrical head doesn't work if it touches the object. The object will be cut unevenly. During cutting, it is difficult for the milling cutter to change direction so it is not convenient for use.

The locking device is used to fix the blade of the milling cutter in a rotary manner. It is rotated to a certain angle to lock or unlock. This locking way is not convenient for use.

The locking seat is connected between the main machine and the milling cutter holder to lock the blade when working. The locking seat comprises a connecting axle therein. The lower end of the connecting axle is connected with the lower output shaft of the main machine and the upper end of the connecting axle is connected with the transmission axle of the blade to function as a middle bridge.

The main machine comprises an outer casing and a motor in the main machine. The output power of the motor brings the blade to rotate through the transmission axle in the locking seat. The main machine and the locking seat are connected through a bolt or an engaging buckle. The connecting way of the bolt is very inconvenient. The connection of engaging buckle is unable to prevent the locking seat from rotating when the milling cutter is running.

Accordingly, the inventor of the present invention has devoted himself based on his many years of practical experiences to solve these problems.

SUMMARY OF THE INVENTION

The primary object of the present invention is to provide a surgical milling cutter which can prevent a cylindrical head from contacting an object to be cut. The surgical milling cutter is nimble to change direction, convenient to lock, and convenient to fix the locking seat and the main machine.

In order to achieve the aforesaid object, the surgical milling cutter comprises a milling cutter holder, a locking device, a locking seat, and a main machine.

The milling cutter holder comprises a fixing seat with a through hole. A finger guider with an L-type holder on a top end thereof is arranged at the upper part of the fixing seat. The distal end of a short side of the L-type holder is provided with a downward projection. The lowest point of the projection is lower than that of a cylindrical head when the milling cutter works normally.

The locking device comprises a protruding platform with a through hole and a bearing arranged on an inner wall of a small cylinder on the protruding platform. A locking sleeve is fitted on the protruding platform. The locking sleeve has a protrusion arranged on the upper part of the inner wall of the locking sleeve and a conical face arranged on the lower part of the inner wall of the locking sleeve. A spring is provided between the bottom of the conical face and an upper bottom face of the protruding platform. A depressor is threadedly connected to an outer wall of the top part of the small cylinder on the protruding platform and presses the protrusion. A conical hole is arranged on the wall of the small cylinder on the protruding platform and communicates with the through hole of the protruding platform. A steel ball is arranged in the conical hole.

The locking seat comprises a bearing disposed on the inner wall of the bottom of the locking seat and a connecting axle having an upper connector and a lower connector to mate with the bearing. The lower part of the connecting axle has a slot. A pin is inserted through the slot to connect the lower connector and the connecting axle. A fourth spring is provided on the connecting axle between the upper connector and the lower connector.

A transmission rod of the milling cuter has a recess corresponding to the conical hole. The lower end of the transmission rod is connected to the upper end of the connecting axle.

The main machine comprises an outer casing and a motor. The upper part of the outer casing of the main machine is provided with a first protruding cylinder having a central through hole. A first bolt is provided to connect a press plate and the outer casing. The inner wall of the first protruding cylinder has an engaging notch. One end of an engaging buckle having a barb is disposed in the engaging notch. A second bolt fitted with a second spring is inserted through the first protruding cylinder and connected with another end of the engaging buckle. The inner wall of the locking seat has a protrusion thereon. The outer casing is provided with two positioning devices. Each positioning device comprises a second protruding cylinder. The second protruding cylinder is disposed in the through hole of the lower part of the first protruding cylinder. A first spring is provided between the first protruding cylinder and the outer casing. The second protruding cylinder is inserted through a hole of the press plate. The hole of the press plate is smaller than the through hole of the lower part of the first protruding cylinder. The bottom of the locking seat has a recess corresponding to the second protruding cylinder.

For the transmission rod to be applied with even force, the locking device comprises two bearings respectively located under the outer wall and above an upper bottom face.

For firmness of the two bearings, a support member is provided between the two bearings.

For convenient connection of a speed reducer, an inner wall of a big cylinder under the protruding platform has inner threads.

A bolt having a through hole is fixed within a cavity of the finger guider. A pressing disk is provided on the upper part of the fixing seat. A nut passes through a hole of the pressing disk and is connected to the bolt.

Alternatively, the lower part of the fixing seat is provided with a finger guider. A T-shaped bolt having a through hole is fixed within a cavity of the finger guider. A pressing disk is provided on the upper part of the fixing seat. A nut passes through a hole of the pressing disk and is connected to the bolt.

For keeping stable working of the milling cutter, the upper part of the finger guide apparatus is provided with a bearing.

To prevent the finger guide from being too nimble, a spring is fitted on the bolt.

For a skidproof effect, the outer surfaces of the fixing seat and the finger guide apparatus each have a skidproof groove.

Preferably, an outer sleeve is fitted on the connecting axle.

Preferably, a lower end face of the lower connector is a "+"-shaped groove.

Preferably, in order to ensure the locking seat is stationary, the two positioning devices are arranged at 180 degrees.

Preferably, for convenient installation, the bottom of the locking seat has four recesses which are equally spaced and disposed on the same periphery.

The protrusion of the present invention is able to prevent an object from contacting the cylindrical head, thus avoiding cutting the object unevenly. Additionally, by driving the L-shaped holder to rotate via the finger guider, the movement direction of the milling cutter can be changed, facilitating the operation. The lower connector of the connecting axle is elastically connected to the output shaft of the main machine so the demand for processing is lower. During use, the extended length of the lower connector of the connecting axle can be adjusted to prolong the service lift of the connecting axle. When the milling cutter is used, the locking seat won't rotate to ensure the safety. The connection of the locking seat and the outer casing of the main machine is simple and quick, and it is convenient for use.

BRIEF DESCRIPTION OF THE DRAWINGS

FIG. 1 is a schematic view according to the preferred embodiment of the present invention;

FIG. 8 is an enlarged view of circle D of FIG. 6; and

FIG. 9 is a top view of FIG. 3.

DETAILED DESCRIPTION OF THE PREFERRED EMBODIMENTS

Embodiments of the present invention will now be described, by way of example only, with reference to the accompanying drawings.

Figure 2:
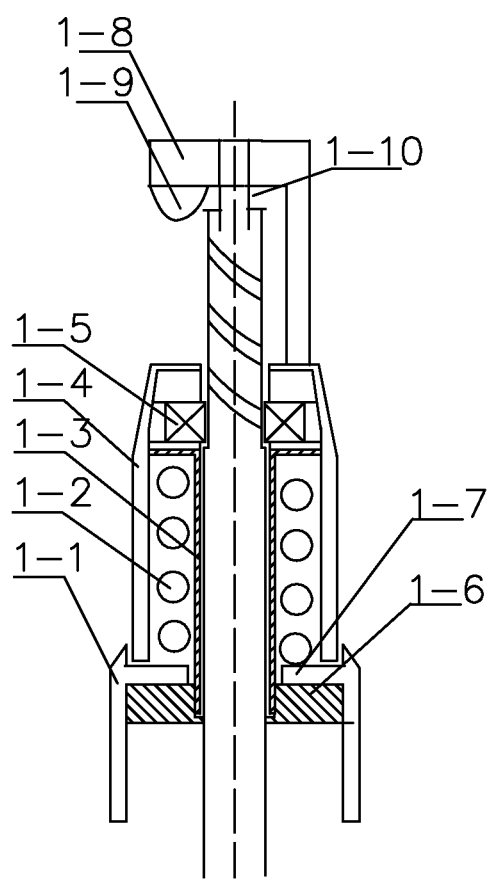
FIG. 2 is a sectional view showing the milling cutter holder of FIG. 1.
Figure 3:
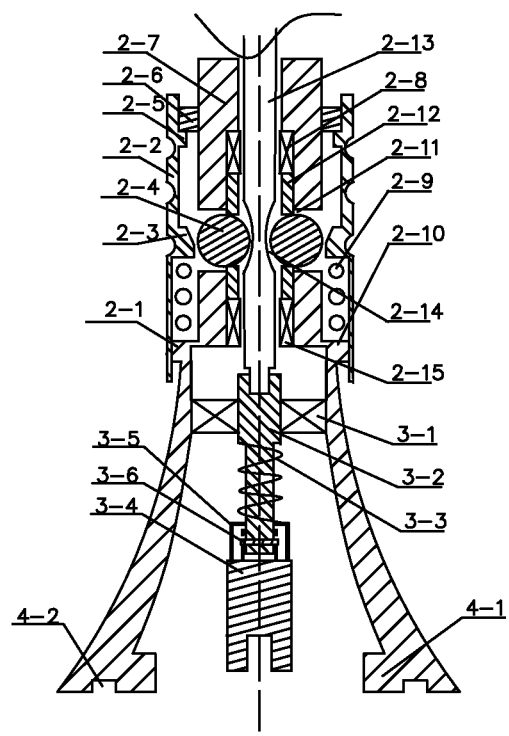
FIG. 3 is a sectional view showing the locking device of FIG. 1
Figure 4:
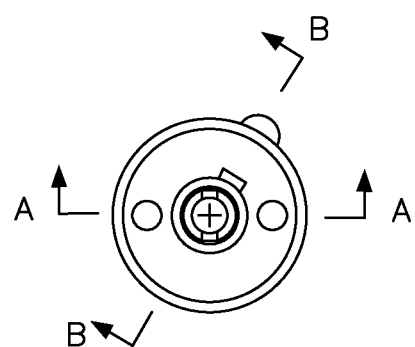
FIG. 4 is a top view of the main machine of FIG. 1.
Figure 5:
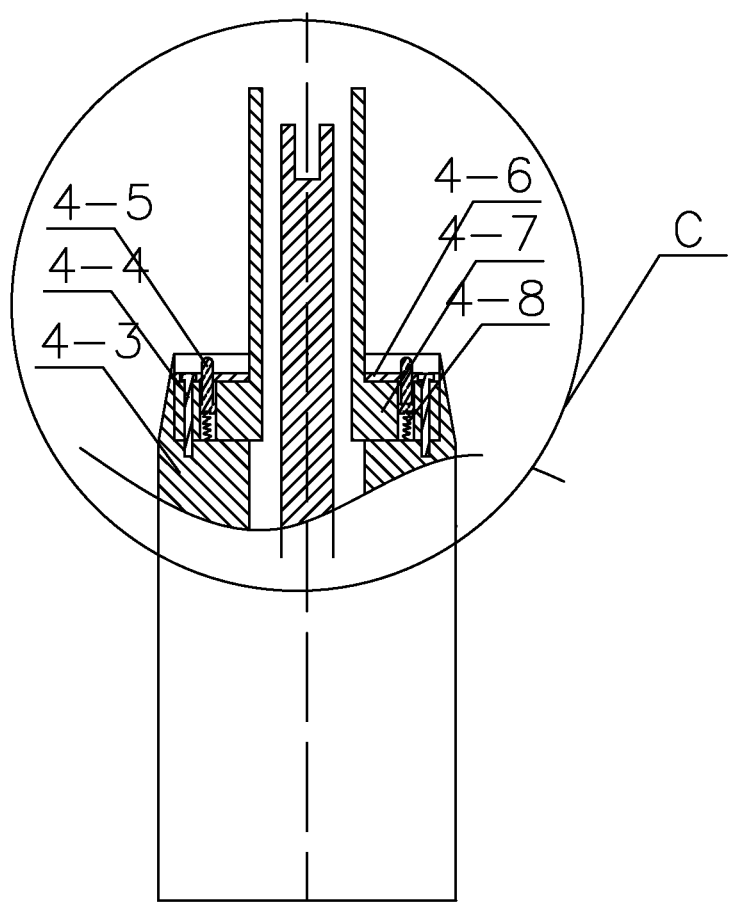
FIG. 5 is a sectional view taken along line A-A of FIG. 4.
Figure 6:
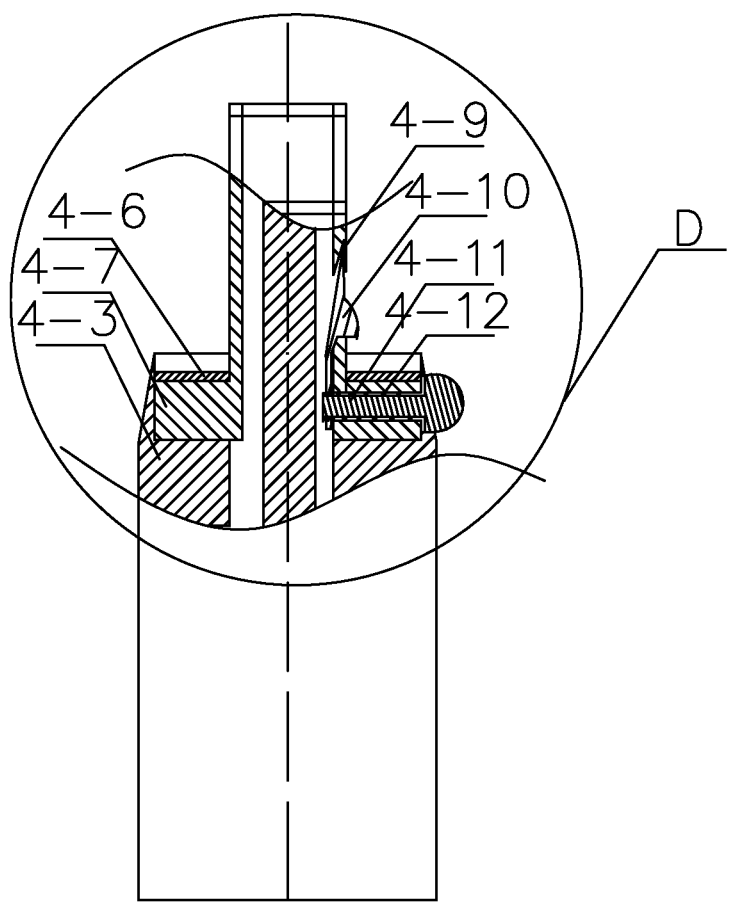
FIG. 6 is a sectional view taken along line B-B of FIG. 4.
Figure 7:
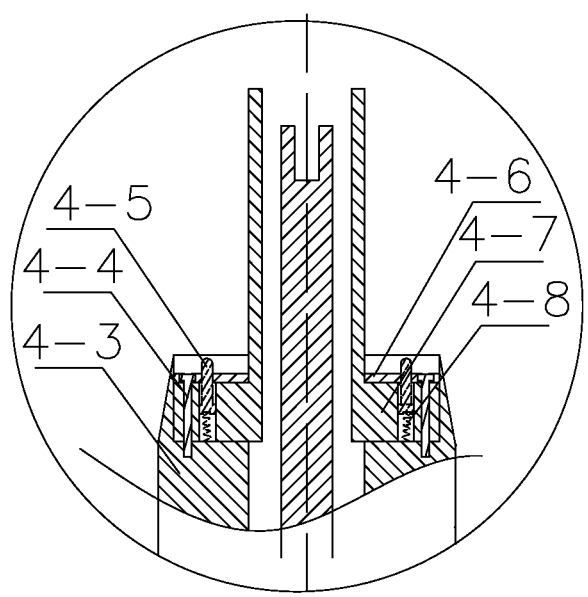
FIG. 7 is an enlarged view of circle C of FIG. 5.

As shown in FIG. 1 to FIG. 9, a surgical milling cutter comprises a milling cutter holder, a locking device, a locking seat, and a main machine. The milling cutter holder comprises a fixing seat (1-1) with a through hole. A finger guider (1-4) with an L-type holder on a top end thereof is arranged at an upper part of the fixing seat (1-1). A distal end of a short side (1-8) of the L-type holder is provided with a downward projection (1-9), and a lowest point of the projection (1-9) is lower than that of a cylindrical head (1-10) when the milling cutter works normally. Thus, the projection (1-9) can prevent an object from contacting the cylindrical head, thereby avoiding occurrence of the phenomenon of unevenly cutting the object. A T-shaped bolt (1-3) with a central through hole is fixed in a cavity of the finger guider (1-4). A pressing disk (1-7) is arranged at the upper part of the fixing seat (1-1). A nut (1-6) is connected to the bolt (1-3) through a hole in the pressing disk (1-7).

The upper part of the finger guider (1-4) is provided with a bearing (1-5). A spring (1-2) is fitted on the bolt (1-3). The outer surfaces of the fixing seat (1-1) and the finger guider (1-4) each have a skidproof groove. The bearing (1-5) makes the milling cutter have a closer force point to ensure stable working of the milling cutter. The spring (1-2) is to ensure a certain force between the finger guider (1-4) and the fixing seat (1-1), preventing the finger guider (1-4) from turning too much to cause an operating error.

When the finger guider (1-4) is turned, the bolt (1-3) and the nut (1-6) are driven to turn. Thus, by driving the L-shaped holder to rotate via the finger guider, the movement direction of the milling cutter can be changed, facilitating the operation.

The locking device comprises a protruding platform (2-1) with a through hole and a bearing (2-8) arranged on an inner wall of a small cylinder on the protruding platform (2-1). In this embodiment, the locking device comprises two bearings (2-8) respectively located under an outer wall (2-7) and above an upper bottom face (2-10). A support member (2-12) is provided between the two bearings (2-8). The two bearings (2-8) can effectively ensure stability of the transmission rod and decrease heat when rotating. The upper bottom face (2-10) is threadedly connected with a tightening member (2-15) to hold against the bearings (2-8) and the support member (2-12) to enhance firmness of the bearings (2-8). A locking sleeve (2-2) is fitted on the protruding platform (2-1). The locking sleeve (2-2) has a protrusion (2-5) arranged on an upper part of an inner wall of the locking sleeve (2-2) and a conical face (2-3) arranged on a lower part of the inner wall of the locking sleeve (2-2). A spring (2-9) is provided between a bottom of the conical face (2-3) and the upper bottom face (2-10) of the protruding platform (2-1). A depressor (2-6) is threadedly connected to the outer wall (2-7) of the top part of the small cylinder on the protruding platform (2-1) and presses the protrusion (2-5). A conical hole (2-11) is arranged on the wall of the small cylinder on the protruding platform (2-1) and communicates with the through hole of the protruding platform (2-1). A steel ball (2-4) is arranged in the conical hole (2-11). The conical hole (2-11) corresponds in position to a recess (2-14) of a transmission rod (2-13) of the milling cuter. An inner wall of a big cylinder under the protruding platform (2-1) has inner threads. In this embodiment, the number of the conical holes (2-11) and the steel balls (2-4) is two as an equivalent change. The number can be three for a better locking effect.

When it is necessary to insert the transmission rod, the locking sleeve is pressed down. At this moment, the conical face is moved down and the steel ball rolls outward. After the transmission rod reaches a desired position, the locking sleeve is released. Through the spring, the locking sleeve ascends and the conical face holds against the steel ball to move inward to engage with the recess of the transmission rod in order to position the transmission rod. This locking way is easy and convenient to lock or unlock, lock firmly, and offer an improved safety.

The locking seat comprises a bearing (3-1) disposed on an inner wall of a bottom of the locking seat and a connecting axle having an upper connector (3-2) and a lower connector (3-4) to mate with the bearing (3-1). A lower part of the connecting axle has a slot. A pin (3-6) is inserted through the slot to connect the lower connector (3-4) and the connecting axle. A fourth spring (3-3) is provided on the connecting axle between the upper connector (3-2) and the lower connector (3-4).

An outer sleeve (3-5) is fitted on the connecting axle. One end of the outer sleeve (3-5) holds against the fourth spring (3-3) and another end of the outer sleeve (3-5) holds against an end face of the lower connector (3-4), such that the lower connector (3-4) has an even force to provide a stable function. The lower end face of the lower connector (3-4) is a cross-shaped groove. Because the top end of the output shaft of the main machine has a " — "-shaped protrusion. Such a configuration is convenient to connect both. When connecting, the lower connector (3-4) is pressed by the output shaft of the main machine so the fourth spring (3-3) will be compressed and the lower connector (3-4) can do a slight adjustment in the slot. This configuration prevents a rigid connection between the connecting axle and the main machine to lower the required precision when processed and to prolong the service life of the equipment.

The connecting structure of the locking seat and an outer casing (4-3) of the main machine of the milling cutter is described hereinafter. The upper part of the outer casing (4-3) of the main machine is provided with a first protruding cylinder (4-7) having a central through hole. A first bolt (4-4) is provided to connect a press plate (4-6) and the outer casing (4-3). The inner wall of the first protruding cylinder (4-7) has an engaging notch (4-9). One end of an engaging buckle having a barb (4-7) is disposed in the engaging notch (4-9). A second bolt (4-11) fitted with a second spring (4-12) is inserted through the first protruding cylinder (4-7) and connected with another end of the engaging buckle. The inner wall of the locking seat has a protrusion (4-1) thereon. The outer casing (4-3) is provided with two positioning devices. Each positioning device comprises a second protruding cylinder (4-5). The second protruding cylinder (4-5) is disposed in the through hole of the lower part of the first protruding cylinder (4-7). A first spring (4-8) is provided between the first protruding cylinder (4-7) and the outer casing (4-3). The second protruding cylinder (4-5) is inserted through a hole of the press plate (4-6). The hole of the press plate (4-6) is smaller than the through hole of the lower part of the first protruding cylinder (4-7). The bottom of the locking seat has a recess (4-2) corresponding to the second protruding cylinder (4-5). The two positioning devices are arranged at 180 degrees. In this embodiment, the bottom of the locking seat has four recesses (4-2) which are equally spaced and disposed on the same periphery.

When in use, the locking seat is connected to the upper part of the outer casing (4-3) and the locking seat is slightly rotated. When the second protruding cylinder (4-5) of the locking seat is aligned align with the recess (4-2) and pressed down, the engaging buckle will engage with the protrusion (4-1). Thus, the locking seat and the outer casing are connected tightly. The second protruding cylinder (4-5) has a positioning function, which can prevent the locking seat from rotating when in use. Through the four recesses (4-2), the locking seat is mounted and positioned by turning 90 degrees only. It is convenient for use. The two positioning devices are to ensure the force effect for the locking seat to be rotated well.

Although particular embodiments of the present invention have been described in detail for purposes of illustration, various modifications and enhancements may be made without departing from the spirit and scope of the present invention. Accordingly, the present invention is not to be limited except as by the appended claims.

What is claimed is:

1. A surgical milling cutter, comprising a milling cutter holder, a locking device, a locking seat, and a main machine;

the milling cutter holder comprising a fixing seat (1-1) with a through hole, a finger guider (1-4) with an L-type holder on a top end thereof being arranged at an upper part of the fixing seat (1-1), a distal end of a short side (1-8) of the L-type holder being provided with a downward projection (1-9), a lowest point of the projection (1-9) being lower than that of a cylindrical head (1-10) when the milling cutter works;

a bolt (1-3) with a central through hole being fixed in a cavity of the finger guider (1-4), a pressing disk (1-7) being arranged at the upper part of the fixing seat (1-1), a nut (1-6) being connected to the bolt (1-3) through a hole in the pressing disk (1-7);

the locking device comprising a protruding platform (2-1) with a through hole and a bearing (2-8) arranged on an inner wall of a small cylinder on the protruding platform (2-1), a locking sleeve (2-2) being fitted on the protruding platform (2-1), the locking sleeve (2-2) having a protrusion (2-5) arranged on an upper part of an inner wall of the locking sleeve (2-2) and a conical face (2-3) arranged on a lower part of the inner wall of the locking sleeve (2-2), a spring (2-9) being provided between a bottom of the conical face (2-3) and an upper bottom face (2-10) of the protruding platform (2-1), a depressor (2-6) being threadedly connected to an outer wall (2-7) of a top part of the small cylinder on the protruding platform (2-1) and pressing the protrusion (2-5), a conical hole (2-11) being arranged on a wall of the small cylinder on the protruding platform (2-1) and communicating with the through hole of the protruding platform (2-1), a steel ball (2-4) being arranged in the conical hole (2-11);

the locking seat comprising a bearing (3-1) disposed on an inner wall of a bottom of the locking seat and a connecting axle having an upper connector (3-2) and a lower connector (3-4) to mate with the bearing (3-1), a lower part of the connecting axle having a slot, a pin (3-6) being inserted through the slot to connect the lower connector (3-4) and the connecting axle, a fourth spring (3-3) being provided on the connecting axle between the upper connector (3-2) and the lower connector (3-4);

a transmission rod (2-13) of the milling cuter having a recess (2-14) corresponding to the conical hole (2-11), a lower end of the transmission rod (2-13) being connected to an upper end of the connecting axle;

the main machine comprising an outer casing (4-3) and a motor, an upper part of the outer casing (4-3) of the main machine being provided with a first protruding cylinder (4-7) having a central through hole, a first bolt (4-4) being provided to connect a press plate (4-6) and the outer casing (4-3), an inner wall of the first protruding cylinder (4-7) having an engaging notch (4-9), one end of an engaging buckle having a barb (4-10) being disposed in the engaging notch (4-9), a second bolt (4-11) fitted with a second spring (4-12) being inserted through the first protruding cylinder (4-7) and connected with another end of the engaging buckle, an inner wall of the locking seat having a protrusion (4-1) thereon, the outer casing (4-3) being provided with two positioning devices, each positioning device comprising a second protruding cylinder (4-5), the second protruding cylinder (4-5) being disposed in a through hole of a lower part of the first protruding cylinder (4-7), a first spring (4-8) being provided between the first protruding cylinder (4-7) and the outer casing (4-3), the second protruding cylinder (4-5) being inserted through a hole of the press plate (4-6), the hole of the press plate (4-6) being smaller than the through hole of the lower part of the first protruding cylinder (4-7), the bottom of the locking seat having a recess (4-2) corresponding to the second protruding cylinder (4-5).

2. The surgical milling cutter as claimed in claim 1, wherein an upper part of the finger guider (1-4) is provided with a bearing (1-5).

3. The surgical milling cutter as claimed in claim 2, wherein a spring (1-2) is fitted on the bolt (1-3).

4. The surgical milling cutter as claimed in claim 3, wherein outer surfaces of the fixing seat (1-1) and the finger guider (1-4) each have a skidproof groove.

5. The surgical milling cutter as claimed in one of claims 1-4, wherein the locking device comprises two bearings (2-8) respectively located under an outer wall (2-7) and above an upper bottom face (2-10).

6. The surgical milling cutter as claimed in claim 5, wherein a support member (2-12) is provided between the two bearings (2-8).

7. The surgical milling cutter as claimed in claim 6, wherein an inner wall of a big cylinder under the protruding platform (2-1) has inner threads.

8. The surgical milling cutter as claimed in claim 7, wherein an outer sleeve (3-5) is fitted on the connecting axle.

9. The surgical milling cutter as claimed in claim 8, a lower end face of the lower connector (3-4) is a cross-shaped groove.

10. The surgical milling cutter as claimed in claim 9, the two positioning devices are arranged at 180 degrees.

11. The surgical milling cutter as claimed in claim 10, wherein the bottom of the locking seat has four recesses (4-2) which are equally spaced and disposed on the same periphery.

\* \* \* \* \*